United States Patent
Danzer et al.

(10) Patent No.: US 8,014,725 B2
(45) Date of Patent: Sep. 6, 2011

(54) METHOD AND DEVICE FOR A SAFETY-ORIENTATED WIRELESS SIGNAL TRANSMISSION

(75) Inventors: Uwe Danzer, Kalchreuth (DE); Robert Kagermeier, Nürnberg (DE); Donal Medlar, Weisendorf (DE); Dietmar Sierk, Erlangen (DE); Reiner Staab, Baiersdorf (DE)

(73) Assignee: Siemens Aktiengesellschaft, Munich (DE)

(*) Notice: Subject to any disclaimer, the term of this patent is extended or adjusted under 35 U.S.C. 154(b) by 587 days.

(21) Appl. No.: 11/660,479

(22) PCT Filed: Aug. 9, 2005

(86) PCT No.: PCT/EP2005/053906
§ 371 (c)(1),
(2), (4) Date: Aug. 8, 2007

(87) PCT Pub. No.: WO2006/018409
PCT Pub. Date: Feb. 23, 2006

(65) Prior Publication Data
US 2008/0034248 A1 Feb. 7, 2008

(30) Foreign Application Priority Data
Aug. 18, 2004 (DE) .......... 10 2004 040 059

(51) Int. Cl.
*H04B 17/00* (2006.01)
(52) U.S. Cl. .......... 455/67.11; 714/1
(58) Field of Classification Search .......... 455/39; 607/27
See application file for complete search history.

(56) References Cited

U.S. PATENT DOCUMENTS

| | | | |
|---|---|---|---|
| 5,243,607 A | | 9/1993 | Masson et al. |
| 5,792,201 A | * | 8/1998 | Causey et al. .......... 607/27 |
| 2001/0051766 A1 | * | 12/2001 | Gazdzinski .......... 600/309 |

FOREIGN PATENT DOCUMENTS

| | | |
|---|---|---|
| DE | 199 46 441 A 1 | 4/2001 |
| DE | 103 12 699 A1 | 11/2003 |
| DE | 103 16 649 A1 | 11/2003 |
| DE | 103 01 225 A1 | 2/2004 |
| EP | 1 107 079 A | 6/2001 |
| EP | 1 391 823 A | 2/2004 |
| JP | 61270935 | 12/1986 |
| WO | WO 03/096298 | 11/2003 |

OTHER PUBLICATIONS

International Search Report dated Dec. 2, 2005.
Written Opinion (with English translation), Jan. 2004.

* cited by examiner

*Primary Examiner* — Temesgh Ghebretinsae
*Assistant Examiner* — David Bilodeau
(74) *Attorney, Agent, or Firm* — Lempia Summerfield Katz LLC

(57) ABSTRACT

A method for safety-directed wireless signal transmission is provided. The method includes duplicating an input signal; supplying each copy of the duplicated input signal within a source unit to a transmitter module over separate, independent software paths; transmitting the copies using the transmitter module over a common wireless transmission link to a receiver module of a sink unit; supplying each transmitted copy within the sink unit over an independent software path to a comparator module; and using the comparator module to test the output copies for consistency with an output signal corresponding to the output copies being generated by the comparator module.

20 Claims, 5 Drawing Sheets

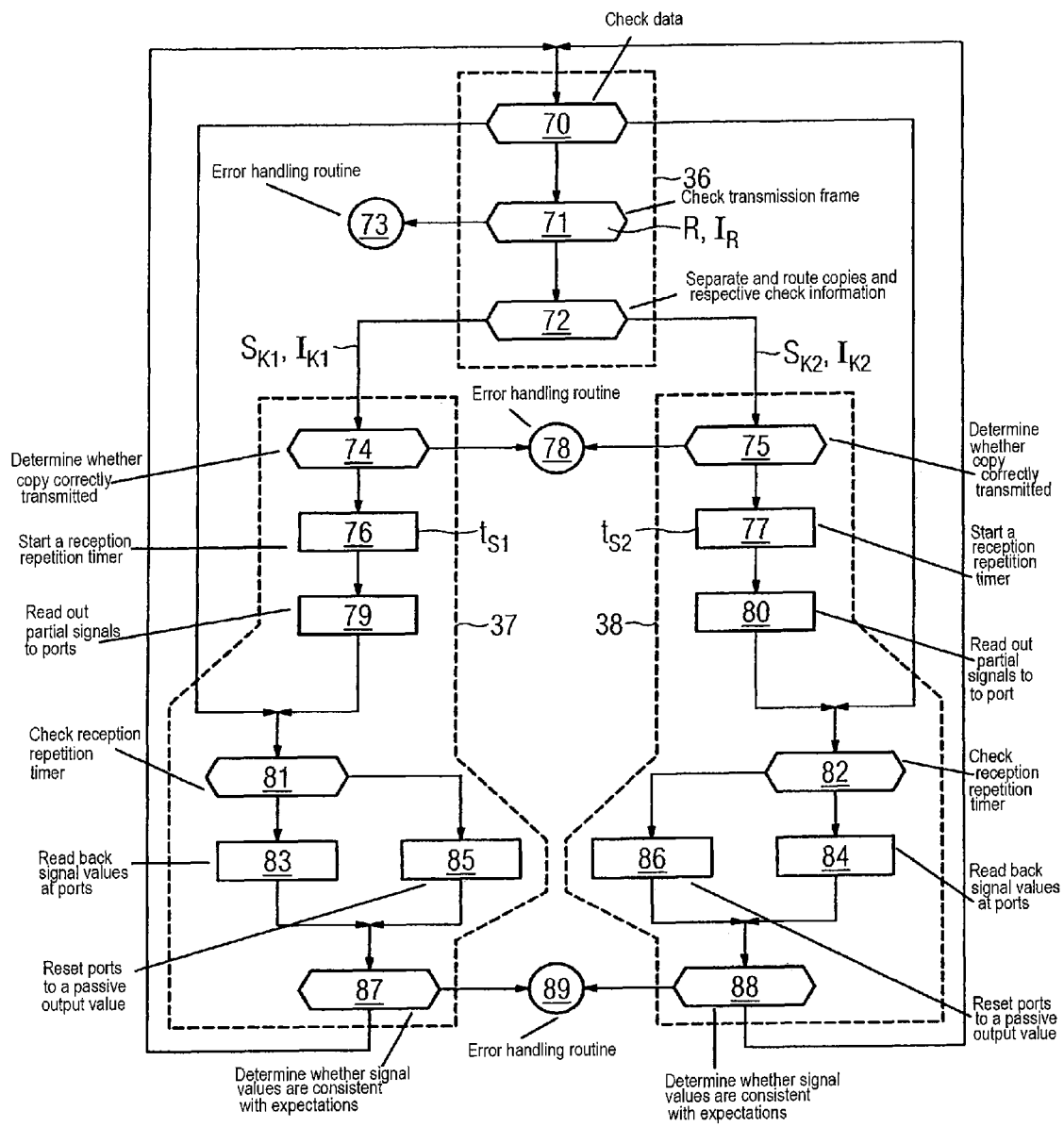

METHOD AND DEVICE FOR A SAFETY-ORIENTATED WIRELESS SIGNAL TRANSMISSION

The present patent document is a §371 continuation of PCT Application Serial Number PCT/EP2005/053906, filed Aug. 9, 2005, designating the United States, which is hereby incorporated by reference. This patent document also claims the benefit of DE 10 2004 040 059.8, filed Aug. 18, 2004.

BACKGROUND

The present embodiments relate to a method for safety-directed wireless signal transmission and to a device for performing the aforesaid method.

The term "signal" is generally understood to refer to an element of information transmitted using electrical, electronic, or electromagnetic devices, such as a control command issued by a command generator to a system controller. This type of signal is described as safety-related when it must be ensured for safety reasons that an error in the transmission of the signal is ruled out or at least detected. A signal should be regarded as safety-related if an error in the signal transmission would result in the risk of damage to objects or injury to persons.

In a medical diagnostic or treatment system, for example, an x-ray system, there are usually a number of safety-related signals to be transmitted. For example, controlling the x-ray emitter of the system and activating the motor drive of a patient table associated with the system represent safety-related signals of this kind. The x-ray emitter or the motor drive of the patient table is controlled in accordance with the control commands initiated by the operating personnel. If the signal transmission fails, in order to prevent injury to the patient being treated and/or the operating personnel, the x-ray emitter or the motor drive should be placed into a safe state without delay.

Generally, a safety-related signal is transmitted by a cabled connection. In order to increase safety, it is customary in this case to transmit the signal redundantly, for example, in parallel over a plurality of independent signal channels. A hybrid transmission structure is also occasionally used. A hybrid transmission structure has a partial signal transmitted in a signal channel in the form of a software telegram, while a further signal channel is a simple physical cable connection. An actual function selection (e.g. raise patient table) is transmitted via the first signal channel, for example, while a general release of the device motor drive (e.g. enable the motor voltage) is effected via the second signal channel.

In order to be able to comply with comparable safety requirements of wireless signal transmission, the transmission structure is traditionally redundant, for example, implemented using two independent infrared transmission links. Wireless signal transmission devices suitable for transmitting safety-related signals usually have a comparatively complex structure.

SUMMARY

The present embodiments may obviate one or more of the drawbacks or limitations of the related art. For example, in one embodiment, a method that allows a reliable signal transmission is realized. In another embodiment, a device is particularly suitable for performing the method.

In one embodiment, an input signal is duplicated. A copy of the input signal generated by said duplication is read into an independent software path of a source unit. Within the source unit, each copy of the input signal is supplied separately on the assigned software path to a common transmitter module that transmits all the copies collectively via a wireless transmission link to a receiver module of a sink unit. Within the sink unit, each copy received is in turn supplied on an independent software path to a comparator module. The comparator module checks the copies with respect to their mutual consistency and, in the event of consistency, outputs an output signal corresponding to the content of the copies.

Different copies are consistent with one another if they correspond to the same signal, for example, contain the same information.

A software path refers to a software module or a number of interdependent software modules, which logically forward a signal during the execution. The external form of the signal may be processed in one or more of the software modules. Two software paths are described as independent of each other when no module of one of the software paths is engaged in data exchange with a module of the other software path. The independence of the parallel software paths implemented in the source unit or in the sink unit prevents an error that occurs during the processing of one software path having an effect on the signal transmission in a parallel software path.

A fully redundant signal transmission is provided when the input signal is duplicated into multiple copies, these copies are routed over independent software paths, and the transmitted copies are compared. A fully redundant signal transmission results in a high probability that any transmission errors will be detected. The single-track embodiment of the actual wireless transmission link may be realized without loss of safety, which in turn permits a comparatively simple hardware structure of the device. The method and the associated device are thus simple while at the same time providing a high level of safety and low risk of failure, and consequently are in particular inexpensive to implement.

In one embodiment, the copy of the input signal routed over each software path of the source unit is protected by generation of check information associated with said copy. In each software path of the sink unit, the copy is checked for transmission errors with the aid of the check information generated on the source side. Check information assigned to the copy takes the form in particular of what is referred to as a CRC (Cyclic Redundancy Code), in particular a 32-bit CRC. No safety requirements need to be placed on the actual wireless signal transmission, for example, on the transmitter or receiver module used because of the source-side generation of the check information and the check made on the sink side. Wireless transmission systems based on any suitable technology and from any manufacturer can be used without adversely affecting the safety of the signal transmission overall.

In one embodiment, the source unit is supplied with the input signal by a signal line, for example, a cable connection. The signal line is implemented in multiple form. The signal line comprises multiple signal channels via each of which a partial signal of the input signal can be supplied. Each partial signal corresponds to a binary switching state.

In one embodiment, the input signal is duplicated on the hardware side, with each signal channel of the signal line being connected to a port of each software path of the source unit. A port generally refers to a binary input and/or output interface of a host controller of the source or sink unit via which a software path implemented in the corresponding host controller reads in or outputs a signal value. An appropriate number of ports are assigned to each software path implemented on the source or sink side.

In one embodiment, the input signal comprises a plurality of partial signals. These partial signals are placed in a different order onto ports of a first software path and corresponding ports of a parallel second software path. Different copies of the input signal consequently receive the partial signals of the input signal in a differently permutated form. The input signal is measured against a predefined port sequence. The permutating duplication of the input signal into the different parallel software paths simplifies the detection of an error in transmission that is software-induced. There is a high probability that any software error acting in the same way on all the software paths would corrupt the mutually corresponding partial signals of the permutated copies in different ways.

In one embodiment, different parallel software paths of the source unit or sink unit are different from one another, for example, are based on different software. Two software modules that correspond to one another in terms of their function but are assigned to different software paths are implemented differently.

In one embodiment, the comparator module is embodied as a hardware comparator, for example, is based on a non-programmable electronic circuit.

In one embodiment, the comparator module outputs an output signal, which produces a safe state of the controlled system, in the event of inconsistency, for example, if two corresponding copies are detected as not being consistent with one another.

In one embodiment, the copies supplied within the source unit from the different software paths are combined for collective transmission to the sink unit in a data structure of a predefined form referred to as a transmission frame. The transmission frame may also contain the optionally generated check information. In one embodiment, source-side generation of associated check information and checking thereof on the sink side is possible.

In one embodiment, both the source unit and the sink unit each include a controller board having a host controller. The software assigned to the corresponding unit is implemented on the host controller. The host controller includes the transmitter module or receiver module. A radio module may be embodied as a combined transmitter/receiver component as the transmitter module of the source unit and as the receiver module of the sink unit. An identical controller board, in terms of the hardware used, may be used both for the source unit and for the sink unit, thereby substantially reducing the manufacturing overhead associated with the fabrication of the device. The different specification of the controller board as a component of the source unit or of the sink unit is handled by a different software configuration and by a different connection arrangement of the controller board.

In one embodiment, a radio module compatible with the Bluetooth standard is used as the radio module on the source and sink side.

In one embodiment, the host controller is assigned a monitoring module (referred to as a "watchdog"). The host controller supplies the monitoring module with a trigger signal at regular intervals. If no trigger signal is received or if the trigger signal is not output within the predefined time interval, the monitoring module detects a malfunction of the host controller and resets the host controller to a defined initial state by a reset command. The monitoring module is preferably provided both on the source side and on the sink side, in particular integrated on the respective controller board of the sink unit and source unit.

In one embodiment, the sink unit is assigned a further monitoring module to which a trigger signal is likewise periodically supplied by the host controller of the sink unit. The monitoring module acts directly on the comparator module and, in the event of a malfunction of the host controller being detected, causes host controller to bring about a safe state of the controlled system by output of a corresponding output signal.

BRIEF DESCRIPTION OF THE DRAWINGS

FIG. 5 is a flow diagram that illustrates one embodiment of a software configuration of the sink unit according to FIG. 2.

DETAILED DESCRIPTION

Figure 1:
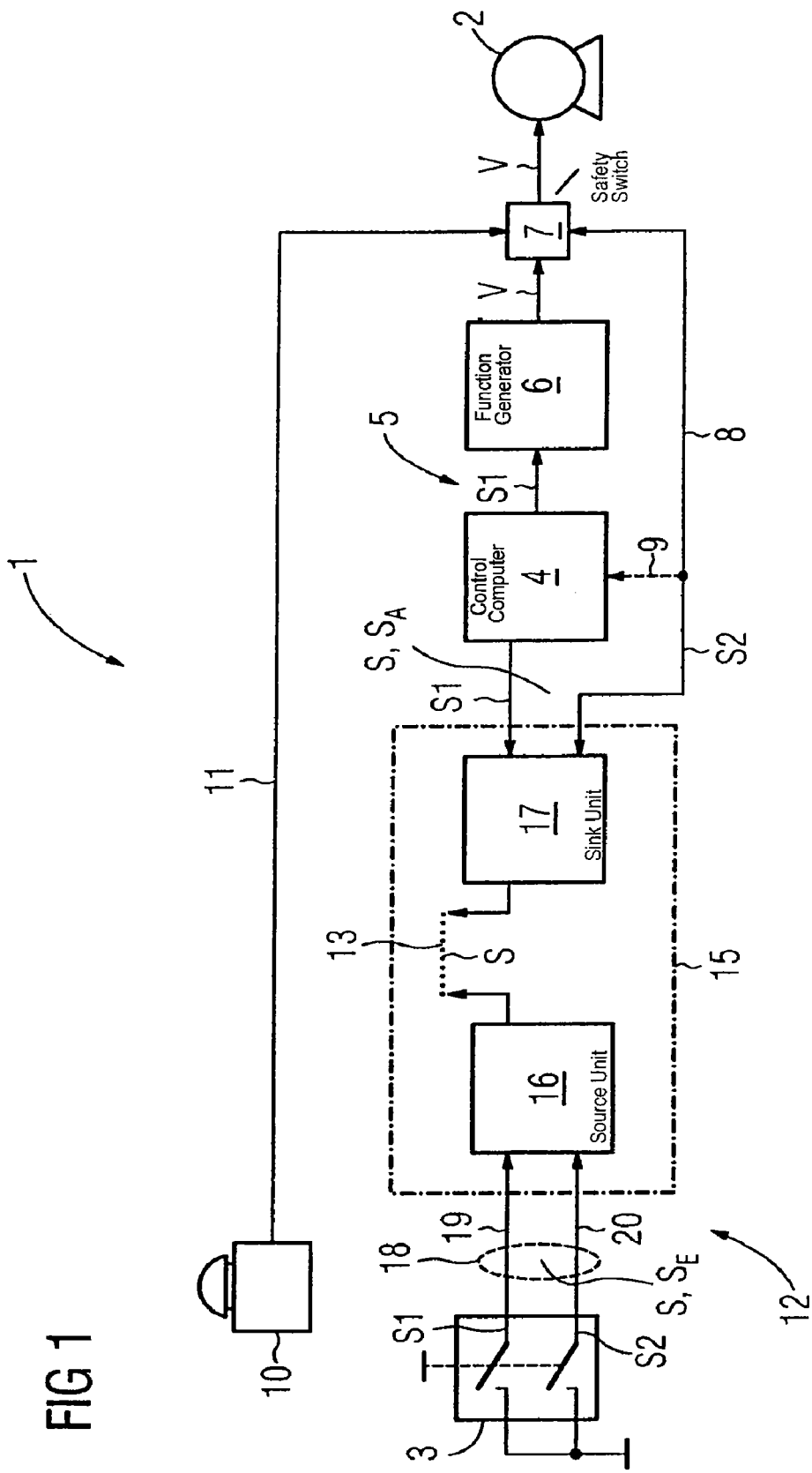
FIG. 1 illustrates one embodiment of medical system having a device connected intermediately between a command generator and a system controller for wireless transmission of a safety-related control signal.

In general, corresponding parts and variables are provided with the same reference numerals/symbols in all the figures.

In one embodiment, as shown in FIG. 1, the system 1, for example, a medical x-ray system, includes a system part 2 that requires being controlled. The system part 2 being, for example, a motor-operated drive that adjust a patient table.

The system 1 includes a command generator 3, which is embodied as a pushbutton switch. A user triggers a safety-related control signal S by actuating the command generator 3. The control signal S includes two partial signals S1 and S2 output by the command generator 3 in parallel and redundantly as electrical switching states. The partial signal S1 represents a function selection, for example, the control command "raise table." The partial signal S1 is supplied to a control computer 4 of a system controller 5. Following appropriate evaluation the control computer 4 outputs the partial signal S1 in the form of a software telegram to a function generator 6 of the system controller 5. The function generator 6 thereupon generates a corresponding supply voltage V for driving the system part 2.

Connected intermediately between the system part 2 and the function generator 6 is a safety switch 7. The second partial signal S2 is supplied in the form of a switching state via an enable line 8 to the safety switch 7. In the activated state, the partial signal S2 acts as an enable signal by triggering a release of the supply voltage V by the safety switch 7. Alternatively, the safety switch 7 forcibly switches off the system part 2 if the partial signal S2 is deactivated. The enable line 8 is routed past the system controller 5 as a physical cable connection in order to guarantee the safety shutdown effected by the partial signal S2 independently of the proper operation of the system controller 5. The proper operation of the enable line 8 is monitored by the control computer 4 via a supervision connection 9.

In one embodiment, the system 1 is assigned an emergency cutoff switch 10. The cutoff switch 10, when actuated, acts directly on the safety switch 7 via a switch line 11 by locking the safety switch 7. The forced shutdown of the system part 2 puts the system 1 into a safe state.

The command generator 3 is part of a mobile control device 12, in particular a portable remote control. The command generator 3 is connected to the system controller 5 via a wireless transmission link 13. For transmission of the control signal S via said wireless transmission link 13, the system 1 includes a device 15. The device 15 includes a source unit 16 assigned to the control device 12 and a sink unit 17 permanently connected to the system controller 5. The signal S to be transmitted is supplied to the source unit 16 by the command generator 3 via a signal line 18 as input signal $S_E$. The signal line 18 includes two signal channels 19 and 20, each of which carries one of the partial signals S1 and S2. The wireless transmission link 13 extends between the source unit 16 and the sink unit 17. The control signal S supplied to the system controller 5 or the safety switch 7 by the sink unit 17 is referred to as the output signal $S_A$.

Figure 2:
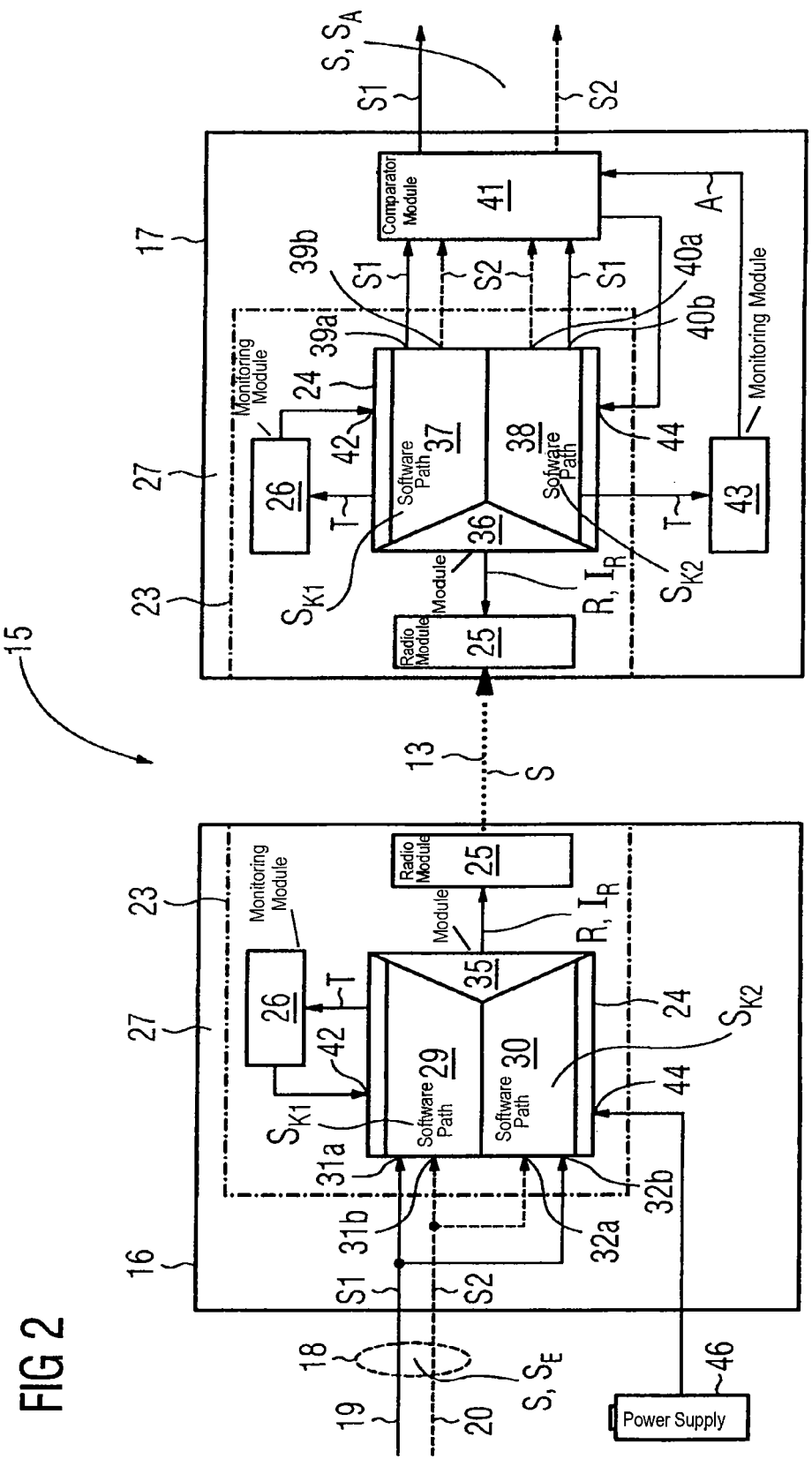
FIG. 2 is a block diagram that illustrates one embodiment of the device according to FIG. 1.

As shown in FIG. 2, the source unit 16 and the sink unit 17 each include a controller board 23 on which a host controller 24 and a radio module 25 operating in Bluetooth technology are mounted. The controller board 23 includes a monitoring module 26, for example, a watchdog that monitors the host controller 24.

The controller board 23 assigned to the source unit 16 and the controller board 23 assigned to the sink unit 17 are identical in design of the hardware. The radio module 25 is a combined transmitter/receiver component. The radio module 25 is used as a transmitter module on the source side and as a receiver module on the sink side. The respective controller board 23 receives the source-side or sink-side specification by a different software configuration, described in more detail below, and by a different connection arrangement, implemented in each case by way of a source-specific or sink-specific base board 27 on which the respective controller board 23 is mounted.

In one embodiment, the control signal S is routed over two independent, for example, logically separated, paths along the transmission path established by the device 15. The input signal $S_E$ is first duplicated and read into the source-side host controller 24 in the form of two copies $S_{K1}$ $S_{K2}$. To allow logically separate processing and forwarding of the respective copy $S_{K1}$ and $S_{K2}$, two independent software paths 29 and 30 are implemented in the host controller 24. The independent software paths 29 and 30, as shown in FIG. 2, are delimited areas of the host controller 24. Each software path 29 or 30 is assigned a number of ports 31a,31b and 32a,32b, respectively, of the host controller 24, via which ports one binary signal value each can be read into the respective software path 29 or 30.

The input signal $S_E$ is duplicated because the first signal channel 19 carrying the partial signal S1 and the second signal channel 20 carrying the partial signal S2 of the signal line 18 are connected to one port 31a, 31b of the first software path 29 and one further port 32a, 32b of the second software path 30. This hardware-side duplication of the input signal $S_E$ has a comparatively high level of fault tolerance. A faulty signal duplication caused by software is categorically excluded.

As can be seen from FIG. 2, the partial signals S1 and S2 are injected in the opposite direction into the software paths 29 and 30, respectively. The first port 31a of the software path 29 is assigned the partial signal S1 and the second port 31b is assigned the partial signal S2. The corresponding ports 32a and 32b of the software path 30 are oppositely assigned the partial signals S2 and S1, respectively. The two copies $S_{K1}$ and $S_{K2}$ of the input signal $S_E$ are conveyed in a different bit sequence on the software paths 29 and 30. Additional reliability is achieved with regard to software-induced transmission errors.

Within each software path 29 and 30, the assigned copy $S_{K1}$ or $S_{K2}$ is protected against transmission errors. Both copies $S_{K1}$, $S_{K2}$ are supplied to the source-side radio module 25 via a module 35. The copies $S_{K1}$ and $S_{K2}$ are "packed" in a common transmission frame R by the module 35. The copies $S_{K1}$ and $S_{K2}$ are transmitted collectively by said source-side radio module 25 to the radio module 25 of the sink unit 17 via the wireless transmission link 13.

The sink-side radio module 25 routes the transmitted copies $S_{K1}$, $S_{K2}$ to the sink-side host controller 24. The transmitted copies $S_{K1}$, $S_{K2}$ are separated in a module 36 and supplied to one of two independent software paths 37 and 38, respectively. Each copy $S_{K1}$ or $S_{K2}$ is checked for transmission errors in the manner described in more detail below. In the case of correct transmission, each copy $S_{K1}$ or $S_{K2}$ is supplied via ports 39a, 39b or 40a, 40b of the sink-side host controller 24 that are assigned to the respective software path 37 or 38 to a comparator module 41 connected downstream thereof.

If no transmission error occurred within the device 15, then, disregarding the transposed order of the partial signals S1 and S2 according to plan, the two copies $S_{K1}$ and $S_{K2}$ must be identical copies of the input signal $S_E$. The same partial signal S1 or S2 has the same value for both copies $S_{K1}$ and $S_{K2}$. This consistency condition is checked in the comparator module 41. The comparator module 41 is a hardware comparator, for example, a non-programmable electronic circuit. The comparator module 41 detects a software-induced malfunction. If the copies $S_{K1}$ and $S_{K2}$ are recognized as consistent, the comparator module 41 outputs an output signal $S_A$ corresponding to the (identical) contents of the copies $S_{K1}$, $S_{K2}$ to the system controller 5. In the event of inconsistency, the comparator module 41 generates an output signal $S_A$ which places the system 1 into the safe state.

In one embodiment, the monitoring module 26 assigned in each case continuously monitors the source-side and the sink-side host controller 24. The assigned host controller 24 supplies the monitoring module 26 with a trigger signal T at predefined regular time intervals. If this trigger signal T is not received or not emitted in the predefined timing pattern, the monitoring module 26 activates a reset port 42 of the respective host controller. The reset port 42 resets the host controller 24 to a defined initial state.

To protect against a dangerous hardware fault of the host controller 24, the sink unit 17 is provided with a second, external shutdown path. The sink unit 17 includes a monitoring module 43 that is supplied with a trigger signal T by the sink-side host controller 24. In another embodiment, the monitoring module 43 acts, not on the host controller 24, but directly on the comparator module 41. In the event of a fault, the monitoring module 43 supplies the comparator module 41 with a shutdown signal A. The shutdown signal A causes the comparator module 41 to place the system 1 into the safe state by outputting a corresponding output signal $S_A$.

The comparator module 41 is monitored either continuously or at regular intervals by the host controller 24 assigned to the sink unit 17. The host controller 24 is connected to the comparator module 41 via a supervision port 44. The corresponding supervision port 44 of the source-side host controller 24 is used for monitoring the power supply of the source unit 16. The source unit 16 or the control device 12 has a power supply 46, in particular a battery or an accumulator, that is independent of the rest of the system 2. If the host controller 24 detects a critical state of said power supply 46, the host controller 24 informs the user, for example, by activating optical and/or acoustic display elements of the control device 12. In one embodiment, the host controller 24 continues to refuse a triggering of a function that in these circumstances would be risky and/or produces a safe state of the system 1.

Figure 3:
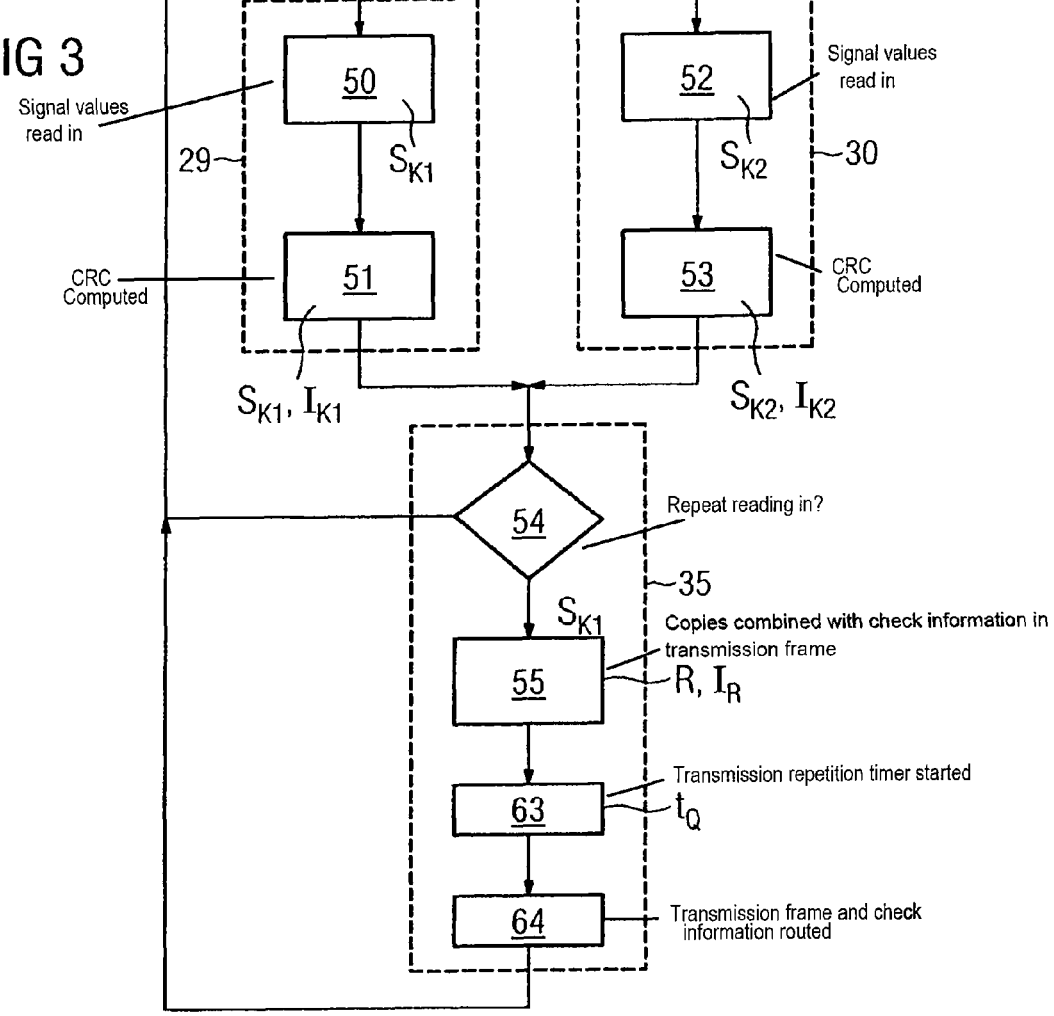
FIG. 3 is a flow diagram that illustrates one embodiment of a software configuration of the source unit according to FIG. 2.

As shown in FIG. 3, the modules 50-55, 63, 64 designate functional components of a piece of software, which are executable in a predefined chronological sequence. The modules 50-55, 63, 64 also represent method steps of the method executed by the software. The same applies to the modules or routines 70-89 introduced in FIG. 5.

As shown in FIG. 3, the parallel software paths 29 and 30 each comprise two sequentially succeeding modules 50 and 51 and 52 and 53, respectively. The signal values of the partial signals S1 and S2 of the copy $S_{K1}$ that are present at the ports 31a and 31b at the time of the query are read in by the first module 50 of the software path 29. In the process of being read in, the signal values are compared bit by bit with corresponding, most recently read-in signal values. It is determined whether the partial signal S1, S2 present at a read-off port 31a, 31b has an unchanged passive ("0") or active ("1") signal value or whether a signal change "0→1" or "1→0" has taken place between the current (present) and the preceding read-in time. A 32-bit CRC that corresponds to the read-in signal values of the copy $S_{K1}$ is computed by the succeeding module 51. The CRC is assigned to the copy $S_{K1}$ as associated check information $I_{K1}$ for the purpose of being able to detect any transmission errors on the sink side.

The module 52 of the parallel software path 30 corresponds in terms of its function to the module 50 and reads in the signal values of the partial signals S2 and S1 of the copy $S_{K2}$ that are present at the assigned ports 32a and 32b, respectively. A CRC is assigned as check information $I_{K2}$ to the copy $S_{K2}$ by the module 53 corresponding in terms of function to the module 51.

The software paths 29 and 30 are independent. No data exchange takes place between the modules 50 and 51 and the modules 52 and 53. A software error of one of the software paths 29, 30 cannot affect the data transmission and data processing in the respective other software path 29, 30.

In one embodiment, the software paths 29 and 30 are implemented dissimilarly. At least one of the modules 50 or 51 of the software path 29 is based on different software, in particular on a different program code, than the functionally corresponding module 52 or 53 of the second software path 30.

In one embodiment, after protecting both copies $S_{K1}$ and $S_{K2}$, a check is made by a module 54 to determine whether a radio transmission is to take place to the sink unit 17. Before initiating a radio transmission, the module 54 checks whether the read-in copies $S_{K1}$ and $S_{K2}$ match one another in terms of the signal values of the partial signals S1 and S2. If necessary, the module 54 checks whether at least one partial signal S1 or S2 is active ("1") or whether a signal change "1→0" has taken place in at least one partial signal S1, S2. When S1="1" OR S2="1" the module 54 checks whether a repetition interval of approx. 50 ms has elapsed since the last radio transmission. The latter condition is checked using a query as to whether a corresponding transmission repetition timer $t_Q$ has timed out, for example, whether the condition $[t_Q=0]$ has been met.

If the above-cited check criteria are satisfied, the module 54 activates a succeeding module 55. Otherwise the module 54 activates the modules 50 and 52 in order to repeat the reading-in operation.

In one embodiment, the same signal value is present at the ports 31a and 32b or 31b and 32a at any given time because of the duplication of the input signal $S_E$. The ports 31a, 31b, 32a, 32b are read off sequentially, for example, at short time intervals due to the program. In the event of a signal occurring during the reading-in operation, different signal values of one or both partial signals S1 and S2 are read into the respective software paths 29 and 30. Such a predictable function-related information discrepancy between the copies $S_{K1}$ and $S_{K2}$ is not evaluated as a transmission error by the module 54. Rather, the reading-in operation is simply repeated in this case.

Figure 4:
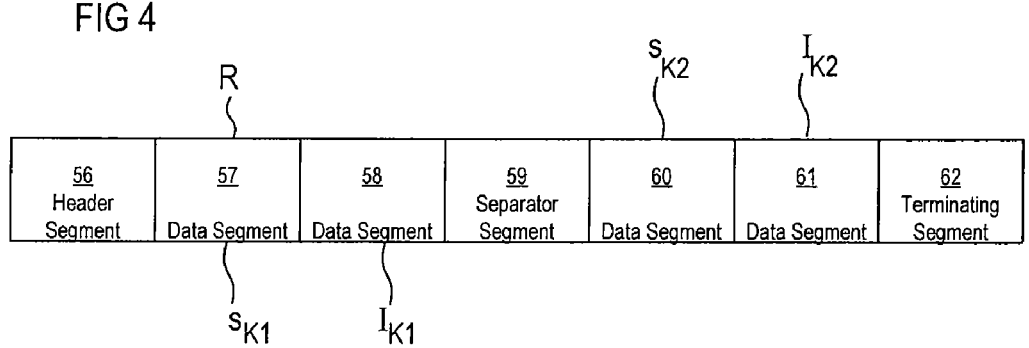
FIG. 4 illustrates one embodiment of the structure of a transmission frame used for transmitting information from the source unit to the sink unit.

If useful information satisfying the aforementioned check criteria is present, the read-in copies $S_{K1}$ and $S_{K2}$ are combined with the respective associated check information $I_{K1}$, $I_{K2}$ in a common transmission frame R by the module 55. The transmission frame R designates a defined data structure. The layout of the data structure is schematically represented in FIG. 4. The transmission frame R includes a header segment 56 of predefined bit length which contains a sequential number and a receiver address assigned to the radio module 25 of the sink unit 17. The header segment 56 may also be referred to as a header. The header segment 56 is followed by two data segments 57 and 58 of predefined bit length. The data segment 57 which includes the copy $S_{K1}$. The data segment 58 includes the associated check information $I_{K1}$. The data segment 58 is followed by a separator segment 59, which includes a characteristic value, in particular "0x00". The separator segment 59 is followed by two data segments 60 and 61. The data segments 60 and 61 may include the content of the copy $S_{K2}$ or the associated check information $I_{K2}$. The data segment 61 is followed by a terminating segment 62, which includes a characteristic value, in particular "0xFF".

In one embodiment, the entire transmission frame R is protected once more by the module 55 by calculation of the associated 32-bit CRC as check information $I_R$.

Once the transmission frame R has been created and the associated check information $I_R$ calculated, the transmission repetition timer $t_Q$ is started by a module 63. A module 64 then routes the transmission frame R together with the associated check information $I_R$ to the radio module 25 for transmission. The reading-in operation is then started once again.

As illustrated by the software configuration according to FIG. 3, an active partial signal (S1="1" OR S2="1"), as long as it is present at the source unit 16, is repeatedly transmitted to the sink unit 17 at regular time intervals predefined by the elapsed time of the transmission repetition timer $t_q$ and continually acknowledged. A constant check of the operation of the source unit 16 is provided for the duration of the active signal state. An active signal state is prevented from being erroneously maintained on the sink side in the event of a possible failure of the source unit 16. An explicit abortion of an active signal state (S1="1→0" OR S2="1→0") is forwarded to the sink unit 17 without delay, in particular independently of the status of the transmission repetition timer $t_Q$.

The software configuration implemented in the sink-side host controller 24 is illustrated in a flow diagram shown in FIG. 5. A check is made by a module 70 to determine whether data has been received by the sink-side radio module 25 and routed to the sink-side host controller 24. In one embodiment, a module 71 determines by checking the receiver address, the sequential number, and the check information $I_R$ whether the received data packet corresponds to an expected transmission frame R and whether the transmission frame R has been correctly transmitted. In one embodiment, the module 71 activates a further module 72. Otherwise the module 71 starts an error handling routine 73.

When the module 71 detects a correct transmission frame R, the module 72 separates the copies $S_{K1}$, $S_{K2}$ and the respective associated check information $I_{K1}$, $I_{K2}$ and routes the copy $S_{K1}$ together with the associated check information $I_{K1}$ to a module 74 of the software path 37. The copy $S_{K2}$ is similarly routed together with the associated check information $I_{K2}$ to a module 75 of the software path 38.

The modules 74 and 75 determine whether the respective copy $S_{K1}$ or $S_{K2}$ was correctly transmitted, for example, is consistent with the respective associated check information $I_{K1}$ or $I_{K2}$. If necessary the module 74 activates a module 76, or the module 75 activates a module 77. In one embodiment, the module 74 or 75, which detects a transmission error, activates an error handling routine 78.

Upon activation, the module 76 or 77 starts an associated reception repetition timer $t_{S1}$ or $t_{S2}$. The activation of the reception repetition timer $t_{S1}$ or $t_{S2}$ indicates that at the activation time or up to the activation time an active signal state S1="1" OR S2="1" was present in the corresponding software path 37 or 38. The reception repetition timer $t_{S1}$ or $t_{S2}$ defines an expected time for the next incoming data packet, which acknowledges or aborts this signal state. If no valid data packet is received within this expected time, an error condition is detected and the system 2 is brought into a safe state.

In one embodiment, as shown in FIG. 3, the reception of a signal acknowledgement or a signal abort is expected within the elapsed time of the transmission repetition timer $t_Q$. The expected time predefined by the elapsed time of the reception repetition timer $t_{S1}, t_{S2}$ is about 100-150 ms and is greater than the elapsed time of the transmission repetition timer $t_Q$ in order to bridge an individual, lost radio transmission without triggering an error.

Following the starting of the respective reception repetition timer $t_{S1}$, the module 76 activates a succeeding module 79. The partial signals S1 and S2 of the copy $S_{K1}$ are read out to the ports 39a and 39b, respectively by the module 79. The module 77 activates a succeeding module 80. The partial signals S2 and 51 of the copy $S_{K2}$ are read out to the ports 40a and 40b, respectively by the module 80.

The method steps described below serve for continuous checking of the signal values output by the sink-side host controller 24. A module 81 checks the software path 37 and a corresponding module 82 of the software path 38 to determine whether the respective reception repetition timer $t_{S1}$ or $t_{S2}$ is still running. In one embodiment, the signal values present at the respective ports 39a, 39b and 40a, 40b are read back by the module 83 and 84, respectively. A check is made to determine whether, as expected, an active signal state ("1") is present at least one of the read-back ports 39a, 39b or 40a, 40b.

If the module 81 or 82 establishes that the respective reception repetition timer $t_{S1}$ or $t_{S2}$ has timed out, the module 81 activates a succeeding module 85 or the module 82 activates a succeeding module 86. The assigned ports 39a, 39b or 40a, 40b are reset to a passive output value ("0") by the respective module 85 or 86. The signal state at the respectively activated ports 39a, 39b or 40a, 40b is read back by the module 85 or 86 to determine whether the resetting of the signal state was performed successfully.

In one embodiment, upon activation of the module 84, the module 86 enables the external comparator module 41. In another embodiment, the comparator module 41 is disabled by the alternative module 86.

Succeeding modules 87 and 88 of the software paths 37 and 38 determine whether the signal values read back by the modules 83 to 86 are consistent with expectations. If necessary the flow diagram according to FIG. 5 is restarted by reactivation of the module 70. In another embodiment, if one of the modules 87 or 88 detects a read error, the module 87 or 88 calls a corresponding error handling routine 89.

As long as no new data is received by the sink unit 17, the module 70 calls the modules 81 and 82 directly so that the program loop defined by the modules 70 and 81 to 88 is executed continuously.

The software paths 37 and 38 are implemented independently and dissimilarly in order to increase the transmission reliability.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A method for safety-directed wireless signal transmission, the method comprising:
   creating, by a command generator, an input signal;
   splitting the input signal into two partial signals with redundant information;
   transmitting the input signal to a source unit via a data transmission line;
   duplicating each of the two partial signals after splitting the input signal into the two partial signals;
   supplying each copy of each duplicated partial signal within the source unit to a transmitter module over separate, independent software paths;
   transmitting the copies using the transmitter module over a common wireless transmission link to a receiver module of a sink unit;
   supplying each transmitted copy within the sink unit over an independent software path to a comparator module; and
   using the comparator module to test the supplied transmitted copies for consistency, with an output signal corresponding to the supplied transmitted copies being generated by the comparator module.

2. The method as claimed in claim 1, comprising:
   generating associated check information on the source side; and
   using the check information to test the copy transmitted to the sink unit for transmission errors in the assigned sink-side software path.

3. The method as claimed in claim 1, comprising: combining the copies supplied from the separate software paths within the source unit in a transmission frame for collective transmission to the sink unit.

4. The method as claimed in claim 3, comprising: protecting the transmission frame by generating check information.

5. The method as claimed by claim 1, wherein duplicating comprising duplicating the input signal comprising the two partial signals such that a first copy and at least one further copy include the two partial signals of the input signal in a different order.

6. A device for safety-directed wireless signal transmission, the device comprising:
   a command generator that creates an input signal and splits the input signal into two partial signals with redundant information;
   a data transmission line that transmits the input signal from the command generator to a source unit, the source unit duplicating each of the two partial signals after the command generator splits the input signal into the two partial signals and comprising a host controller having at least two independent software paths that separately supply a copy of the duplicated input signal to a common transmitter module; and a sink unit that comprises a second host controller having at least two independent software paths that separately output copies received by a common receiver module to a comparator module connected downstream thereof, wherein the source unit and sink unit are connected via a wireless transmission link, and wherein the comparator module is configured to test the output copies for consistency and generate an output signal corresponding to the output copies.

7. The device as claimed in claim 6, wherein each source-side independent software path of the at least two source-side independent software paths is configured to generate associated check information and to check an assigned copy for transmission errors with the aid of the associated check information generated on the source side.

8. The device as claimed in claim 6, comprising: a signal line having two signal channels, the signal line being configured to supply the input signal to the source-side host controller and each signal channel of the two signal channels being connected to a port of each source-side independent software path of the at least two source-side independent software paths.

9. The device as claimed in claim 8, wherein each of the two signal channels is configured to carry one of the two partial signals of the input signal, and wherein each of the two signal channels is connected in a different order to ports of a first source-side independent software path of the at least two source-side independent software paths and corresponding ports of a second source-side independent software path of the at least two source-side independent software paths.

10. The device as claimed in claim 6, wherein the comparator module is a hardware comparator.

11. The device as claimed in claim 6, wherein the comparator module is configured to output an output signal that produces a safe state when an inconsistency is detected.

12. The device as claimed in claim 6, wherein the source unit includes a controller board that includes the host controller and the common transmitter module, and wherein the sink unit includes a controller board that includes the second host controller and the common receiver module.

13. The device as claimed in claim 12, wherein the common transmitter module and the common receiver module both comprise a radio module that is a combined transmitter/receiver component.

14. The device as claimed in claim 13, wherein the controller board assigned to the source unit and the controller board assigned to the sink unit have identical electronic structures.

15. The device as claimed in claim 13, wherein the radio module is a Bluetooth module.

16. The device as claimed in claim 6, wherein a monitoring module assigned to at least one host controller of the host controller and the second controller is configured to monitor an operation of the at least one host controller with the aid of a trigger signal transmitted at regular intervals to the monitoring module by the at least one host controller and to reset the at least one host controller to a defined initial state in the event of an error.

17. The device as claimed in claim 6, wherein the sink unit includes a monitoring module that monitors a proper operation of the second host controller with the aid of a trigger signal transmitted at regular intervals to the monitoring module by the second host controller and is configured to activate the comparator module directly by outputting an output signal that produces a safe state.

18. The device as claimed in claim 6, wherein each software path of the at least two source-side independent software paths and the at least two sink-side independent software paths includes at least one software module, with at least two mutually functionally corresponding software modules of parallel software paths being implemented differently.

19. The device as claimed in claim 9, wherein the comparator module is configured to output an output signal that produces a safe state when an inconsistency is detected.

20. The device as claimed in claim 19, wherein the source unit includes a controller board that includes the host controller and the common transmitter module, and wherein the sink unit includes a controller board that includes the second host controller and the common receiver module.

* * * * *

UNITED STATES PATENT AND TRADEMARK OFFICE
CERTIFICATE OF CORRECTION

| | | |
|---|---|---|
| PATENT NO. | : 8,014,725 B2 | Page 1 of 1 |
| APPLICATION NO. | : 11/660479 | |
| DATED | : September 6, 2011 | |
| INVENTOR(S) | : Uwe Danzer et al. | |

It is certified that error appears in the above-identified patent and that said Letters Patent is hereby corrected as shown below:

In the claims:

Column 10, claim 5, line 2, please delete "comprising" before "duplicating" and insert --comprises-- before "duplicating."

Signed and Sealed this
Twenty-eighth Day of February, 2012

David J. Kappos
*Director of the United States Patent and Trademark Office*

UNITED STATES PATENT AND TRADEMARK OFFICE
CERTIFICATE OF CORRECTION

PATENT NO.        : 8,014,725 B2                                               Page 1 of 1
APPLICATION NO.   : 11/660479
DATED             : September 6, 2011
INVENTOR(S)       : Uwe Danzer et al.

It is certified that error appears in the above-identified patent and that said Letters Patent is hereby corrected as shown below:

In the claims:

Column 10, line 54 (claim 5, line 2) please delete "comprising" before "duplicating" and insert --comprises-- before "duplicating."

This certificate supersedes the Certificate of Correction issued February 28, 2012.

Signed and Sealed this
Twenty-seventh Day of March, 2012

David J. Kappos
*Director of the United States Patent and Trademark Office*